US012566182B2

(12) United States Patent
Nandi et al.

(10) Patent No.: US 12,566,182 B2
(45) Date of Patent: Mar. 3, 2026

(54) POINT OF CARE DEVICE, METHOD AND KIT INVOLVING CLUB CELL PROTEIN 16 AS A MARKER FOR SILICOSIS

(71) Applicant: INDIAN COUNCIL OF MEDICAL RESEARCH, New Delhi (IN)

(72) Inventors: Shyam Sundar Nandi, Mumbai (IN); Upendra P. Lambe, Mumbai (IN); Kamlesh Sarkar, Ahmedabad (IN); Jagadish Mohan Deshpande, Mumbai (IN); Sonali Ankush Sawant, Mumbai (IN)

(73) Assignee: INDIAN COUNCIL OF MEDICAL RESEARCH, New Delhi (IN)

( * ) Notice: Subject to any disclaimer, the term of this patent is extended or adjusted under 35 U.S.C. 154(b) by 790 days.

(21) Appl. No.: 17/904,201

(22) PCT Filed: Mar. 31, 2021

(86) PCT No.: PCT/IN2021/050328
§ 371 (c)(1),
(2) Date: Aug. 12, 2022

(87) PCT Pub. No.: WO2021/199081
PCT Pub. Date: Oct. 7, 2021

(65) Prior Publication Data
US 2023/0077769 A1 Mar. 16, 2023

(30) Foreign Application Priority Data
Mar. 31, 2020 (IN) .............................. 202011014266

(51) Int. Cl.
*G01N 33/68* (2006.01)

(52) U.S. Cl.
CPC ... *G01N 33/6884* (2013.01); *G01N 2333/785* (2013.01); *G01N 2800/12* (2013.01)

(58) Field of Classification Search
None
See application file for complete search history.

(56) References Cited

U.S. PATENT DOCUMENTS

2020/0116737 A1* 4/2020 Masters ............. G01N 33/6893
2021/0208165 A1* 7/2021 Chen .................. G01N 33/6893

FOREIGN PATENT DOCUMENTS

WO 01/55723 A1 8/2001

OTHER PUBLICATIONS

Wang (J. Occup Environ Med 2007 49:834-839) (Year: 2007).*
Anfossi (Biosensor 2019 vol. 9, total 14 pages). (Year: 2019).*
Hayatbakhsh et al. (Reports of Biochem & Mol. Biology 2019 8: 9-14) (Year: 2019).*

(Continued)

*Primary Examiner* — Changhwa J Cheu
(74) *Attorney, Agent, or Firm* — Workman Nydegger

(57) ABSTRACT

The present invention provides a device and method based on lateral flow immunoassay for CC16 semi-quantification in serum sample. A novel membrane based semi quantitative detection of physiological/pathological levels of CC16 in the serum has been provided. The device of the present invention provides affordable and easy to use strip-based screening approach for early detection of silicosis using CC16 as a biomarker.

3 Claims, 2 Drawing Sheets

| Figure | Description | Figure | Description |
|---|---|---|---|
| | Positive control | | Negative control |
| | Observation: | | Observation: |
| | One band at the control line | | One band at the control line |
| | All the three bands at the test line | | No band at the test line |
| | Sample 1 | | Sample 2 |
| | CC16 Concentration: | | CC16 Concentration: |
| | 11.59 ng/ml | | 25.69 ng/ml |
| | Observation: | | Observation: |
| | One band at the control line | | One band at the control line |
| | All the three bands at the test line | | All the three bands at the test line |
| | Sample 3 | | Sample 4 |
| | CC16 Concentration: | | CC16 Concentration: |
| | 12.53 ng/ml | | 7.82 ng/ml |
| | Observation: | | Observation: |
| | One band at the control line | | One band at the control line |
| | All the three bands at the test line | | Two bands at the test line |
| | Sample 5 | | Sample 6 |
| | CC16 Concentration: | | CC16 Concentration: |
| | 4.57 ng/ml | | 0.19 ng/ml |
| | Observation: | | Observation: |
| | One band at the control line | | One band at the control line |
| | One band at the test line | | No bands at the test line |

(56)     References Cited

OTHER PUBLICATIONS

Pandey, Jai Krishna et al., "Biomarkers: A Potential Prognostic Tool for Silicosis", Indian Journal of Occupational and Environmental Medicine, Dec. 2012, vol. 16, Issue 3, pp. 101-107.

Parekh, Gita, "Leukocyte-Mediated Degradation of Lung Extracellular Matrix & Serum Molecules in Chronic Inflammatory Disease, as Discerned Through Urinary Biomarkers", Cardiff University Thesis, Sep. 2018.

Gulumian, M. et al. "Mechanistically Identified Suitable Biomarkers of Exposure, Effect, and Susceptibility for Silicosis and Coal-Worker'S Pneumoconiosis: A Comprehensive Review", Journal of Toxicology and Environmental Health, Part B: Critical Reviews, 2006, 9:5, pp. 357-395.

Upaassana, Vinitha Thiyagarajan et al., "High sensitive lab-on-a-chip (LOC) immunoassay for early diagnosis of respiratory disease caused by respirable crystalline silica (RCS)", Analytical Chemistry, ACS Publications, Apr. 23, 2019.

Broeckaert, F. et al., "Clara Cell Secretory Protein (CC16): Features as a Peripheral Lung Biomarker", Annals New York Academy of Sciences, Feb. 2000, 923(1), pp. 68-77.

Sajid, Muhammad et al., "Designs, formats and applications of lateral flow assay: A literature review", Journal of Saudi Chemical Society, Sep. 2, 2014.

Bernard, A. et al., "Biomonitoring of early effects on the kidney or the lung", The Science of the Total Environment 199, 1997, pp. 205-211.

* cited by examiner

| Sr. No. | Figure | Description | Sr. No. | Figure | Description |
|---|---|---|---|---|---|
| 1 | | Negative control<br><br>Observation:<br><br>Control line: One band observed<br>Test line: No band observed | 2 | | CC16: 0 to 6 ng/ml<br>(Suspected moderate to<br>advance silicosis)<br><br>Observation:<br><br>Control line: One band observed<br>Test line: Single band observed |
| 3 | | CC16: 6.1 to 9 ng/ml<br>(Suspected early Silicosis)<br><br>Observation:<br><br>Control line: One band observed<br>Test line: Two bands observed | 4 | | CC16: > 9 ng/ml and above<br>(healthy person with normal<br>X ray)<br><br>Observation:<br><br>Control line: One band observed<br>Test line: Three bands observed |

Figure 1

| Figure | Description | Figure | Description |
|---|---|---|---|
| | Positive control<br><br>Observation:<br><br>One band at the control line<br><br>All the three bands at the test line | | Negative control<br><br>Observation:<br><br>One band at the control line<br><br>No band at the test line |
| | Sample 1<br><br>CC16 Concentration:<br><br>33.39 ng/ml<br><br>Observation:<br><br>One band at the control line<br><br>All the three bands at the test line | | Sample 2<br><br>CC16 Concentration:<br><br>25.69 ng/ml<br><br>Observation:<br><br>One band at the control line<br><br>All the three bands at the test line |
| | Sample 3<br><br>CC16 Concentration:<br><br>12.51 ng/ml<br><br>Observation:<br><br>One band at the control line<br><br>All the three bands at the test line | | Sample 4<br><br>CC16 Concentration:<br><br>7.82 ng/ml<br><br>Observation:<br><br>One band at the control line<br><br>Two bands at the test line |
| | Sample 5<br><br>CC16 Concentration:<br><br>4.57 ng/ml<br><br>Observation:<br><br>One band at the control line<br><br>One band at the test line | | Sample 6<br><br>CC16 Concentration:<br><br>0.19 ng/ml<br><br>Observation:<br><br>One band at the control line<br><br>No bands at the test line |

Figure 2

POINT OF CARE DEVICE, METHOD AND KIT INVOLVING CLUB CELL PROTEIN 16 AS A MARKER FOR SILICOSIS

FIELD OF THE INVENTION

The present invention generally lies in the field of lateral flow immunoassay-based techniques. The invention relates to a point of care rapid detection kit for semi quantitative estimation of CC16 in human samples. This can be used for screening of silicosis samples.

BACKGROUND OF THE INVENTION

Silicosis is an irreversible occupational ailment of respiratory system caused by the invasion of lung tissue (parenchyma) to dust consisting of crystalline silica or silicon dioxide of micro respirable size (less than 10µ in diameter). Individuals with various exposure interval ranging from 2 to 15 years or more in the industries like mines, stone quarry, agate, construction sites and non-metallic product manufacturing units for example refractory (articles with heat resistant ability), ceramic, glass, mica, and structural clay are more prone to silicosis. These micro-particles get trapped in the interstitial lung collagen tissue resulting in fibrosis of lung. Therefore, it becomes one of the major occupational health hazards for the construction and mine workers. Regrettably, most of the silicosis cases remain undiagnosed or misdiagnosed at an early stage due to asymptomatic nature of the initial stage of the disease, lack of suitable biomarker for early detection, poor health-seeking behavior of the workers and poor occupational health care delivery service at the working areas, particularly in unorganized sectors.

Patients with silicosis are prone to develop pulmonary tuberculosis also called as silico-tuberculosis, probably due to destruction of alveolar macrophages. Shafiei M et al. (2019) also reports that silico-tuberculosis is critical in community settings among workers and employees exposed to silica dust.

Nandini et al. (2016) discusses that as silicosis is incurable, clinical management includes removing the worker from the industry and giving symptomatic treatment. Public health goals are to detect early cases through monitoring of currently and formerly exposed workers, to establish surveillance programmes, to slow progression and to reduce disability. Differential diagnosis is difficult unless the physician is aware of the occupational history of silica exposure, which is very subjective in nature. Also, it becomes very difficult to differentiate between silicotic nodules and tuberculous infiltration in radiography. Additionally, the difficulty in isolation of *Mycobacterium tuberculosis* from sputum of silico-tuberculosis patients as silicotic fibrosis prevents discharge of *Mycobacterium* in the sputum, making the situation more difficult. Hence, a suitable biomarker is required for early detection of suspected silicosis. This will augment in the prophylaxis and control of advanced silicosis and silico-tuberculosis patients.

Clinically, the diagnosis of silicosis is performed by chest radiology. X-ray showing pathognomonic opacities along with the history of crystalline silica dust exposure. Diagnosis is invariably made at an advanced or end stage when it is irreversible. Moreover, silicosis patients are susceptible to develop tuberculosis. Therefore, a suitable biomarker for early detection of suspected silicosis is needed.

A number of anti-inflammatory biomarkers for early diagnosis of silicosis have been tested, but most of these were found to be non-specific and hence conferred unsuitable for diagnosis of lung related pathologies. Club cell protein (CC16) is secreted by Club cells of Broncho-alveolar epithelial tissue of lung. CC16 is proposed to be a peripheral marker of respiratory epithelial injury that protects respiratory tract against oxidative stress-induced inflammation and passively diffuses in bronchoalveolar-blood bather to plasma. CC16 deficiency has been reported to be associated with an increased susceptibility of lung to viral infections and oxidative stress in experimental rodent model. This protein functions as anti-inflammatory, immunosuppressive, anti-fibrosis agent also in the removal of unwanted impurities in the respiratory tract. The CC16 also has effect of pulmonary surfactant and participates in a series of many physiological and pathological processes of lungs. The serum concentration of CC16 can be used to decipher the degree of respiratory tract injury and lung alveolar capillary barrier integrity at an early stage. Though the exact physiological mechanism of CC16 remains unknown, but evidences suggest significant reduction of CC16 in silica dust-exposed workers with no change in respiratory symptoms, normal chest radiology and lung function tests indicates that CC16 could be an early asymptomatic detection tool for suspected silicosis and silica-exposed population at risk.

Research shows that many chronic pulmonary inflammatory diseases such as anthraco-silicosis, chronic obstructive pulmonary disease (COPD), asthma etc. causes depletion of CC16. COPD is a condition of lungs in which the pathogenesis is still not very clear. The main reason being progressive symmetric erythrokeratodermia develops during COPD causing hindrance in the airway. The etiological factors can be many such as breathing in of particulate dust particles, bacterial infections or smoking. In all types of cases, Clara cells are degenerated and reduced in number resulting in decreased levels of CC16 in Broncho-alveolar lavage fluid (BALF) and serum. The anti-inflammatory and protective effect of CC16 on the airway epithelium is gone resulting into inflammation of lungs. In case of per-acute or acute attacks, the CC16 level increases and results in the repair of the airway epithelium. But in cases of chronic exposures, the CC16 levels reduce gradually resulting in the chronic inflammation which is ultimately leading towards fibrosis of lungs.

As endogenic anti-inflammatory substance, CC16 has very important immunomodulatory and anti-inflammatory action in lung. One of its anti-inflammatory pathway mechanisms suppresses phosphide enzyme A2 (PLA2) activity. The PLA is a very active enzyme in all keratocytes. According to this, the keratocytes can be divided into, secretory type which is calcium dependent and endocytosis type which is calcium independent. PLA 2 is on activation along with its regular functions such as lipid production, platelet activation also activates inflammatory cytokines. Intracellular toxins or pollutants can trigger PLA2 and can aggravate inflammatory response.

Although the CC16 has inbuilt anti-inflammatory activity, but still the exact molecular mechanism of its activity is not known yet. But according to some studies, the anti-inflammatory activity is shown by suppressing PLA2 activity, restriction of arachidonic acid metabolism and down regulation of interleukins and prostaglandins.

At present-day, the CC16 detection is performed with commercially available enzyme linked immunosorbent assays (ELISA) of clinical field application. The available commercial assays are very expensive and cannot be afforded by the daily wage workers. Thus, there is a need for economical, user friendly and rapid detection devices and methods which does not require expensive instrumentation or specialized skills for testing and analysis.

The present invention thus provides a lateral flow immunoassay based, a point of care device and a kit that can be particularly employed for assaying a sample suspected to have silicosis which is simple to operate, involves use of pollution free reagents and is cost effective as well. The device of the present invention is for screening of selected population with occupational silica dust exposure history for early detection of silicosis. Once the subject is identified as suspected silicosis, confirmation must be done by chest X-ray or CT-scan. Wide application of this device among vulnerable population is expected to reduce both silicosis as well as silico-tuberculosis.

OBJECTIVES OF THE INVENTION

An essential objective of the present invention is to provide a lateral flow assay-based device or strip for detection of Club cell protein 16 for screening of suspected silicosis.

Another objective of the present invention is to provide a method for semi-quantitative detection of Club cell protein 16 using the device of the present invention.

Yet another objective of the present invention is to provide a low cost, user friendly, point of care kit for semi-quantitative detection of Club cell protein 16.

SUMMARY OF THE INVENTION

The present disclosure overcomes one or more shortcomings of the prior art and provides additional advantages discussed throughout the present disclosure. Additional features and advantages are realized through the techniques of the present disclosure. Other embodiments and aspects of the disclosure are described in detail herein and are considered a part of the claimed disclosure.

The present invention provides a point of care device and method based on gold nanoparticles based lateral flow assay for CC16 quantification in serum sample. A novel membrane based semi quantitative detection of physiological as well as pathological level of CC16 in the serum has been provided. The device of the present invention is affordable and easy to use strip based diagnostic test for CC16 (for early detection of suspected silicosis through periodic screening among occupationally silica dust exposed workers).

The present invention thus provides an easy and economical device and method for quantifying the abovementioned biomarker protein for assessing degree of lung fibrosis & healthy lung due to continuous exposure to silica dust while working. The level of protein can be measured in the serum. Decrease in the expression of the CC16 protein is an indicator of lung related pathology.

BRIEF DESCRIPTION OF ACCOMPANYING FIGURES AND TABLES

The embodiments of the disclosure itself, as well as a preferred mode of use, further objectives and advantages thereof, will best be understood by reference to the following detailed description of an illustrative embodiment when read in conjunction with the accompanying drawings as listed below:

FIG. 1 illustrates interpretation of results for CC16 lateral flow assay.

FIG. 2 shows results of six tested samples along with the controls. The details of the samples are listed in the Table 2.

Table 1 depicts the clinical significance of concentration of CC16 in serum.

Table 2 shows performance evaluation of Lateral flow assay for semi-quantitation of CC16 by comparison with ELISA.

Table 3 depicts interpretation of performance evaluation of lateral flow assay for semi-quantification of CC16.

Table 4 shows the details of the samples depicted in FIG. 2.

The figures depict embodiments of the disclosure for purposes of illustration only. Further, the experimental results and/or data mentioned/depicted in the figures and in the present disclosure are merely for purpose of illustration only and thus, various set-ups, embodiments and its implementation details described in this disclosure are not limited to the exemplifies details. One skilled in the art will readily recognize from the following description that alternative embodiments of the methods illustrated herein may be employed without departing from the principles of the disclosure described herein for screening of selected population with occupational silica dust exposure history for early detection of silicosis.

DETAILED DESCRIPTION OF THE INVENTION

The foregoing broadly outlines the features and technical advantages of the present disclosure in order that the detailed description of the disclosure that follows may be better understood. It should be appreciated by those skilled in the art that the conception and specific embodiment disclosed may be readily utilized as a basis for modifying the disclosed methods or for carrying out the same purposes of the present disclosure.

The novel features which are believed to be characteristic of the disclosure, both as to its organization and method of operation, together with further objects and advantages will be better understood from the following description when considered in connection with the accompanying figures. It is to be expressly understood, however, that each of the figures and examples is provided for the purpose of illustration and description only and is not intended as a definition of the limits of the present disclosure.

The present invention provides a cost effective, user friendly device and method for rapid quantification of CC16 for early detection of suspected silicosis in serum sample among occupationally exposed workers. A novel membrane based semi-quantitative lateral flow assay-based detection of physiological levels of CC16 in the serum has been provided. Since the disease is irreversible and existing X-ray based diagnosis usually detects silicosis cases in an advanced stage, said lateral flow assay-based detection of CC16 helps in an early detection through periodic screening and thereby saving the victim from premature disability & death caused by silicosis.

A high-risk subject in accordance with the present invention includes but is not limited to occupationally silica dust exposed workers.

In an embodiment, the present invention relates to double antibody sandwich method: antibody coated membrane or strip and detection by gold nanoparticles (GNPs) labelled antibody. In the immuno-chromatographic assay (Lateral flow) for detection of CC16, a strip pre-coated with polyclonal anti-CC16 antibody is used to interact with serum CC16. Later, the detection is performed with anti-CC16 monoclonal antibody labelled with gold nanoparticles. The semi quantification is performed by coating the antibody at three levels on the immuno-chromatography strips along with one topmost control line. The upper most line i.e., control line is coated with the 0.2 µg/µl goat anti-mouse antibody while the lower three lines i.e., test lines are to be coated with 0.2 µg/µl polyclonal rabbit anti-CC16 antibody. The control line is indicative of valid reaction. If the control line does not appear, the reaction is invalid. Serum CC16 is aimed for periodic screening of silica dust exposed workers (occupational exposure) for early detection of suspected silicosis. Earlier study conducted by the applicant conclusively evidenced that most healthy person have their serum CC16 values 12 ng/ml or above as lower cut off value (average=15 ng/ml). Similarly, most x-ray confirmed silicosis subjects had their serum cc16 values 9 ng/ml or lower. Hence upper cut off value for early silicosis has been considered at 9 ng. Subsequent study had shown that moderate silicosis starts from 6 ng/ml as upper cut off value whereas advanced silicosis had an upper cut off value of 3 ng/ml among x-ray confirmed silicosis subjects. It may be noted all silicosis patients mandatorily need to be confirmed by chest x-ray.

Considering the fact of x-ray confirmation, serum CC16 of 6.1 to 9 ng/ml has been considered as early silicosis. Subjects having >9 ng/ml are either healthy or in very early stage of silicosis which will not cast shadow in x-ray chest/HRCT, making it difficult to diagnose as silicosis as per existing law of the country.

In an embodiment, the device of the present invention is for screening of selected population with occupational silica dust exposure history for early detection of silicosis. Once the subject is identified as suspected silicosis, confirmation must be done by chest X-ray or CT-scan. Wide application of this device among vulnerable population is expected to reduce both silicosis as well as silico-tuberculosis.

Considering the abovementioned assumptions, if the serum CC16 concentration is <6 ng/ml, one red colored band is detected. If the serum CC16 concentration is in the range of 6 to 9 ng/ml then the assay produces two bands and if the serum CC16 concentration is >9 ng/ml, the assay produces three bands. One control band is observed at the control line irrespective of the CC16 concentration present in the serum.

In an embodiment, membrane-based device in the form of a strip is used for detection and semi-quantification of CC16, which is a biomarker for early detection of suspected silicosis due to continuous exposure to silica dust while working. Anti CC16 antibody is coated on a membrane to react with CC16 biomarker from serum. The detection and semi quantification is performed with appropriately labelled anti CC16 antibody.

In an embodiment, the present invention provides a point of care device, in the form of a lateral flow immunoassay-based strip for semi-quantitative detection of CC16 in a test sample, comprising:
- a) a conjugate pad comprising a membrane-based coated with an anti-CC16 antibody;
- b) a sample pad to which a test sample is applied;
- c) a common absorbant pad, and
- d) a result window/detection pad for visualizing the results based on appearance of colored band on said pad, wherein said strip is fixed inside a plastic cassette, and wherein on addition of test sample to the sample pad, appearance of one red colored band implies suspected silicosis and serum CC16 concentration <6 ng/ml, appearance of two bands implies moderate suspected silicosis and serum CC16 concentration between 6 to 9 ng/ml, and appearance of three bands imply no silicosis and serum CC16 concentration >9 ng/ml.

In another embodiment, the conjugate pad of the said point of care device is made up of glass fiber.

In yet another embodiment, CC16 monoclonal antibodies are conjugated with gold nanoparticles.

In still another embodiment, the present invention provides a method based on lateral flow immunoassay for assaying a sample for semi-quantification of CC16, comprising:
- a) injecting a test sample into the sample pad; and
- b) performing semi-quantitative analysis for assessing the concentration or the level and severity of a condition associated with the concentration of CC16 based on presence of one or more colored bands, wherein the serum CC16 concentration <6 ng/ml and appearance of one red colored band implies suspected silicosis; the serum CC16 concentration between 6 to 9 ng/ml and appearance of two bands imply moderate suspected silicosis and the serum CC16 concentration >9 ng/ml and production of three bands imply no silicosis.

In yet another embodiment of the claimed method, the condition associated with CC16 concentration in serum is silicosis.

In a further embodiment of the device claimed or the method of the present invention, the test sample is serum sample from a high-risk subject.

In still another embodiment, the present invention provides a kit for assaying a sample for assessing the concentration of CC16, comprising:
- i) a point of care device of the present invention;
- ii) an instruction manual including the indication that the serum CC16 concentration of <6 ng/ml and appearance of one red colored band implies suspected silicosis; the serum CC16 concentration between 6 to 9 ng/ml and appearance of two bands imply moderate suspected silicosis and the serum CC16 concentration of >9 ng/ml and production of three bands imply no silicosis.

In another embodiment, the present invention provides a method for preparing the point-of-care device of the present invention, comprising:
- a) conjugating gold nanoparticles (GNPs) with anti-CC16 antibodies to make the conjugate pad; and
- b) assembling said sample pad, conjugate with a common absorbant pad with the overlap so as to obtain a strip and packing the same in a plastic cassette.

In a further embodiment, the device or the kit of the present invention is used for screening of silicosis in a subject.

EXAMPLES

Material and Methods

Test material, human blood sample was collected from venous blood of patients with high risk and suspected exposure to silica. The most preferred samples may be 2-3 ml of blood from venipuncture collected into a vacutainer without EDTA The serum was separated from the blood by allowing the blood to coagulate by keeping the test tube in slanting position. This was followed by centrifuging the blood at 5000 relative centrifugal force for 5 minutes to separate serum from the coagulated blood. Efforts are being taken to develop the same technology by using the whole blood directly in the strip, where no separation of serum is required.

Assay primarily involved collection of blood from clinical subjects and separation of serum from the blood and refrigeration at −20° C. Lateral flow strips (MDI membrane technologies, Ambala India) were coated with 0.2 μg/μl rabbit anti-CC16 polyclonal antibody (PeproTech, USA). Gold nanoparticles (PeproTech, USA) were conjugated with anti-CC16 mouse monoclonal antibody (ThermoFisher scientific, USA).

10 μl of serum sample was run on the test strip and results were observed.

Reagent Compositions

For dilution of antibody: 10 mM Tris.HCl pH 8
1. 1% Bovine serum albumin (BSA) dissolved in 10 mM Tris.HCl pH 8
2. For dilution of CC16 protein: 1×PBS pH 7.2
3. 0.1M Potassium carbonate ($K_2CO_3$) to change pH of GNPs
4. Wash buffer: 900 μl of 10 mM Tris HCl pH8, 100 μl of 1% BSA in (10 mM Tris HCl pH 8) and 50 μl of Tween-20

Recombinant CC16 Protein

The recombinant protein commercially procured from *BioVendor—Laboratorni medicina a.s., Czech Republic* (Cat. No. RD 191022200) was used as the master standard in this assay. The club cell protein is a 9.2 kDa protein consisting of 80 amino acids.

Conjugation of Antibody with Gold Nanoparticles (GNPs)

A 2 ml volume of mono dispersed GNPs solution (40 nm, negative charge) was taken in two separate sterile 1.5 ml tubes (1 ml in each tube). GNPs solution was centrifuged at 13200 rpm at 4° C. for 5 min. 500 μl of supernatant was discarded from each tube and the soft pellets were re-suspended in the remaining solutions.

Contents of the two tubes were pooled together. The pH of the pooled GNPs solution was adjusted to 9 using 0.1M $K_2CO_3$ solution. Generally, 12-15 μl of 0.1 M $K_2CO_3$ solution is enough to adjust the pH to 9 for 1 ml GNPs solution. 10 μg of anti-CC16 mAb in 10 mM Tris HCl (pH 8) was added to the above prepared 1 ml GNPs solution drop wise with gentle mixing by inverting 5 times.

The tube was incubated at room temperature for 10 minutes. Bovine serum albumin (BSA) at a final concentration of 0.025% (W/V) was dissolved in 10 mM Tris HCl (pH 8). Said buffer was added drop wise for blocking unoccupied sites on the GNPs mixed by inverting the tube 5 times. The tube was incubated at room temperature for 10 minutes. The reaction mixture was centrifuged at 4000×g for 1 hour at 4° C.

Maximum possible supernatant was discarded carefully without disturbing the soft pellet. The soft pellet was re-suspended in 50 μl of 10 mM Tris-HCl pH 8 with 0.1% (w/v) final concentration of BSA. The conjugate containing tube was covered with aluminium foil and stored between 2-8° C. until further use. The working solution of the conjugate was diluted 1:5 times (1 μl conjugate+4 μl wash buffer) in wash buffer.

Selection of Membrane for Coating Antibody

A wide variety of membranes are available to meet the requirements of different tests. These membranes are directly cast on a transparent polyester backing to improve the handling strength. Standard polyester film is 100 μm thick. The wicking rate is an important characteristic of nitrocellulose membrane (NCM) for lateral flow tests and primarily determines the reaction kinetics. The wicking rate is an important characteristic of nitrocellulose membrane (NCM) for lateral flow tests and primarily determines the reaction kinetics. The wicking rates of blocked membranes will depend on blocking protocol. In the present assay, CNPF-SN12-L2-P25 10 μm membrane was used. The CNPF-SN12 membrane is associated with lower protein binding. The L2 is associated with Laminate with NC membrane mounted on it and adhesive placed for sample pad and absorbent pad. The 10 μm is the porosity of the membrane.

Assembly and Setting Up the Strip

The CNPF-SN12-L2-P25 10 μm membrane strips were used for this assay. The NCM was marked with a pencil with the width of 0.5 cm. Each strip was cut with the help of a clean and sharp pair of scissors.

Coating Strips with Rabbit Anti-CC16 Polyclonal Antibody

Four lines, 0.5 cm from each other were marked on the stencil and used as a tool to help the coating of the antibody on the NCM. The antibody was diluted in 10 mM Tris-HCl pH 8 to make the concentration of 0.2 μg/μl for coating on the surface of each strip.

For coating of the strip, a glass capillary tube was dipped in the antibody solution which allows the capillary tube to suck in a volume of diluted antibody by capillary action. The capillary tube was then moved on the strip with a swift hand movement over the nitrocellulose membrane strip to coat the antibody on the membrane, wherein The upper most band (control band) was coated with the Goat anti-mouse antibody 0.2 μg/μl.

The lower three bands (test bands) were coated with Rabbit anti-CC16 antibody polyclonal.

Test line 1: Rabbit anti-CC16 Antibody 0.2 μg/μl

Test line 2: Rabbit anti-CC16 Antibody 0.2 μg/μl

Test line 3: Rabbit anti-CC16 Antibody 0.2 μg/μl

The strips were dried at 37° C. for 1 hour.

Sample Application and Testing

The strips were placed at a horizontal surface. 10 μl of each serum sample was loaded on each strip and allowed to flow through the membrane. 10 μl of working GNPs+anti-CC16 mAb conjugate was loaded and allowed to flow through the membrane strip. Again 10 μl of wash buffer was allowed to flow through the membrane to wash off the extra GNPs+anti-CC16 mAb conjugate from the strip. Then the number of bands were observed on the lateral flow strip.

Results and their Interpretation

Interpretation of the results is as follows: the control line is indicative of valid reaction. If the control line does not appear, the reaction is invalid. If the serum CC16 concentration is <6 ng/ml, one red colored band is detected. If the serum CC16 concentration is in the range of 6 to 9 ng/ml then the assay produces two bands and if the serum CC16 concentration is >9 ng/ml, the assay produces three bands. One control band is observed at the control line irrespective of the CC16 concentration present in the serum (FIG. 1).

Clinical significance of the results obtained in terms of the number of bands visualized and their relation with CC16 concentration is depicted in the table 1 below:

TABLE 1

| Sr. No. | CC16 concentration (ng/ml) | Number of bands in lateral flow assay | Clinical Significance |
|---|---|---|---|
| 1 | 0 to 6 ng/ml | 1 | Suspected silicosis (Lung damage) |
| 2 | 6.1 to 9 ng/ml | 2 | Moderate suspected silicosis (Mild lung damage) |
| 3 | >9 ng/ml | 3 | Healthy person |

The CC16 concentration of 0 to 6 ng/ml which is depicted by 1 band in serum samples are suspected for silicosis or other lung damage. They should be further investi-gated by chest X-ray and if required CT scan and need immediate treatment.

The CC16 concentration of 6.1 to 9 ng/ml which is depicted by 2 band in serum samples are suspected for moderate silicosis. These persons should consult doctor and other investigation is required if suggested by the doctor.

The CC16 concentration >9 ng/ml which is depicted by 3 band in serum samples are healthy person.

Performance Evaluation of the Assay

The performance of the assay was evaluated by testing 47 serum samples. The serum samples were also tested by commercially available ELISA kit. The comparative evalu-ation was performed by estimating CC16 concentration by ELISA and numbers of bands on lateral flow assay (Table 2). The comparative evaluation of ELISA and lateral flow strip test showed that if the serum CC16 concentration is <6 ng/ml, one red colored band is detected at the test line. If the serum CC16 concentration is in the range of 6 to 9 ng/ml then the assay produces two bands at the test line and if the serum CC16 concentration is >9 ng/ml, the assay produces three bands at the test line. One control band is observed at the control line irrespective of the CC16 concentration present in the serum.

TABLE 2

| Sr. No. | Sample ID | CC16 con ng/ml | strip bands on test lines | Strip match |
|---|---|---|---|---|
| 1 | 02-D | 4.7 | 2 | Y |
| 2 | 06-D | 7.5 | 2 | Y |
| 3 | 07-D | 9.5 | 3 | Y |
| 4 | 18-D | 8.2 | 2 | Y |
| 5 | 16-D | 7.7 | 2 | Y |
| 6 | 17-D | 8.2 | 2 | Y |
| 7 | 19-D | 12.5 | 3 | Y |
| 8 | 21-D | 10.2 | 3 | Y |
| 9 | 28-D | 16.6 | 3 | Y |
| 10 | 110-D | 7.4 | 2 | Y |
| 11 | 111-D | 9.5 | 3 | Y |
| 12 | 119-D | 14.6 | 3 | Y |
| 13 | 13D | 16.2 | 3 | Y |
| 14 | 30D | 14.8 | 3 | Y |
| 15 | 31D | 9.5 | 3 | Y |
| 16 | 38D | 15.6 | 3 | Y |
| 17 | 102D | 6.9 | 2 | Y |
| 18 | 104D | 7.8 | 2 | Y |
| 19 | 107D | 15.1 | 3 | Y |
| 20 | 112D | 10.6 | 3 | Y |
| 21 | 114D | 8.4 | 3 (2) | Y |
| 22 | 116D | 11.6 | 3 | Y |
| 23 | 125D | 10.2 | 3 | Y |
| 24 | 133D | 16.2 | 3 | Y |
| 25 | 136D | 5.6 | 1 | Y |
| 26 | 1 | 8.909091 | 2 | Y |
| 27 | 2 | 11.81818 | 3 | Y |
| 28 | 3 | 9.545455 | 3 | Y |
| 29 | 4 | 25.69318 | 3 | Y |
| 30 | 5 | 6.215909 | 2 | Y |
| 31 | 6 | 10.46591 | 3 | Y |
| 32 | 7 | 0.193182 | 1 | Y |
| 33 | 8 | 7.829545 | 2 | Y |
| 34 | 9 | 8.579545 | 2 | Y |
| 35 | 10 | 21.11364 | 3 | Y |
| 36 | 11 | 4.579545 | 1 | Y |
| 37 | 12 | 14.13636 | 3 | Y |
| 38 | 13 | 10.29545 | 3 | Y |
| 39 | 14 | 14.94318 | 3 | Y |
| 40 | 15 | 23.60227 | 3 | Y |
| 41 | 16 | 33.39773 | 3 | Y |
| 42 | 17 | 4.272727 | 1 | Y |
| 43 | 18 | 10.46591 | 3 | Y |
| 44 | 19 | 5.034091 | 1 | Y |

TABLE 2-continued

| Sr. No. | Sample ID | CC16 con ng/ml | strip bands on test lines | Strip match |
|---|---|---|---|---|
| 45 | 20 | 12.51136 | 3 | Y |
| 46 | 21 | 12.85227 | 3 | Y |
| 47 | 22 | 14.68182 | 3 | Y |

TABLE 3

| CC16 range | Nos. | Nos. of bands on the strip | | | |
|---|---|---|---|---|---|
| ng/ml | Samples | NIL | ONE | TWO | THREE |
| <=1 | 1 | 0 | 1 | 0 | 0 |
| 1.1 to 2 | 0 | 0 | 0 | 0 | 0 |
| 2.1 to 3 | 0 | 0 | 0 | 0 | 0 |
| 3.1 to 4 | 0 | 0 | 0 | 0 | 0 |
| 4.1 to 5 | 3 | 0 | 2 | 1 | 0 |
| 5.1 to 6 | 2 | 0 | 2 | 0 | 0 |
| 6.1 to 7 | 2 | 0 | 0 | 2 | 0 |
| 7.1 to 8 | 5 | 0 | 0 | 5 | 0 |
| 8.1 to 9 | 5 | 0 | 0 | 5 | 0 |
| 9.1 to 10 | 4 | 0 | 0 | 0 | 4 |
| 10.1 TO 11 | 6 | 0 | 0 | 0 | 6 |
| 11.1 TO 12 | 2 | 0 | 0 | 0 | 2 |
| 12.1 TO 14 | 3 | 0 | 0 | 0 | 3 |
| 14.1 TO 16 | 7 | 0 | 0 | 0 | 7 |
| >16 | 7 | 0 | 0 | 0 | 7 |
| Total | 47 | | 5 | 15 | 27 |

TABLE 4

| Sr. No. | Serum number | CC16 concentration | Number of bands observed on test line |
|---|---|---|---|
| 1 | P | Known positive serum | Three bands observed |
| 2 | N | FBS | No bands observed |
| 3 | 1 | 33.39 ng/ml | Three bands observed |
| 4 | 2 | 25.69 ng/ml | Three bands observed |
| 5 | 3 | 12.51 ng/ml | Three bands observed |
| 6 | 4 | 7.82 ng/ml | Two bands observed |
| 7 | 5 | 4.57 ng/ml | One band observed |
| 8 | 6 | 0.19 ng/ml | No band observed |

Further, FIG. 2 shows results of six tested samples along with the controls. The details of the samples are listed in the Table 4.

Advantages

The method of the present invention is quite robust and requires minimal amount of sample i.e., about 10 µl.

The device of the present invention is a point of care device and thus can be used without high operational requirements.

The time for diagnosis is about 10 minutes whereas the conventional tests take a minimum of about 3 hours depending on the techniques used.

There is no need of any technical expertise or training to diagnose the patients with the present kit as the diag-nosis is based only on visualization of bands i.e., presence or absence and number of bands on the strips.

The working cost of the strip is about 100-125 (INR) as against 600 (INR) for the conventional diagnostic tests.

The invention claimed is:

1. A method based on lateral flow immunoassay for screening silicosis by semi-quantification of human serum CC16 protein, the method comprising:

a. loading a test sample onto a sample pad, wherein the test sample comprises CC16 protein;

b. providing a conjugate pad, wherein the conjugate pad comprises gold nanoparticle labelled anti-CC16 monoclonal antibody, wherein the gold nanoparticle labelled anti-CC16 monoclonal antibody conjugates with the CC16 protein of the test sample to form a complex;

c. providing a nitrocellulose membrane, wherein the nitrocellulose membrane is coated with polyclonal anti-CC16 antibody on three test lines in a concentration of 0.2 µg/µl at each of the three test lines and a control line, wherein the control line comprises a goat anti mouse antibody, wherein the complex is drawn to nitrocellulose membrane by capillary action to conjugate with the polyclonal anti-CC16 antibody to obtain coloured bands at each of the three test lines;

d. visualizing the coloured bands at each of the three test lines through a detection window; and thereby semi quantitatively analysing a concentration of the CC16 protein in the test sample to assess severity of silicosis based on presence of one or more coloured bands at the three test lines, wherein the CC16 protein concentration of less than 6 ng/ml results in one coloured band on the three test lines, and implies suspected silicosis; the CC16 protein concentration in between 6 to 9 ng/ml results in two coloured bands on the three test lines, and implies moderate suspected silicosis; and the CC16 protein concentration greater than 9 ng/ml results in three coloured bands on the three test lines, and implies no silicosis.

2. The method as claimed in claim 1, wherein the test sample is a human serum sample from a high-risk subject.

3. A kit for assessing severity of silicosis, the kit comprising:

a point of care device, wherein the device is in the form of a lateral flow immunoassay for semi-quantitative detection of CC16 protein in a test sample; and an instruction manual, wherein the instruction manual instructs that if one coloured band is observed on three test lines through a detection window, it implies suspected silicosis; if two coloured bands are observed on the three test lines through the detection window, it implies moderate suspected silicosis, and if three coloured bands are observed on the three test lines through the detection window, it implies no silicosis, wherein the CC16 protein concentration of less than 6 ng/ml results in one coloured band on the three test lines; the CC16 protein concentration in between 6 to 9 ng/ml results in two coloured bands on the three test lines; and the CC16 protein concentration greater than 9 ng/ml results in three coloured bands on the three test lines, wherein the point of care device comprises a plastic cassette, wherein the plastic cassette comprises:

a sample pad, wherein the sample pad is configured to receive the test sample;

a conjugate pad comprising gold nanoparticle labelled anti-CC16 monoclonal antibody, a nitrocellulose membrane coated with a polyclonal anti-CC16 antibody on the three test lines, and a goat anti mouse antibody on a control line;

an absorbant pad, and a detection window for visualizing the results.

*    *    *    *    *